United States Patent [19]
Irsch et al.

[11] Patent Number: 5,916,818
[45] Date of Patent: Jun. 29, 1999

[54] ISOLATION AND CHARACTERIZATION OF ALLERGEN-BINDING CELLS FOR DIAGNOSIS OF HYPERSENSITIVITY

[75] Inventors: Johannes Irsch, Cologne; Stefan Miltenyi, Bergisch Gladbach; Andreas Radbruch, Berlin, all of Germany

[73] Assignee: Miltenyi Biotec GmbH, Bergisch Gladbach, Germany

[21] Appl. No.: 09/037,126

[22] Filed: Mar. 9, 1998

Related U.S. Application Data

[63] Continuation of application No. 08/660,035, Jun. 6, 1996, Pat. No. 5,786,161.

[51] Int. Cl.[6] .......................... G01N 33/53; G01N 33/553
[52] U.S. Cl. .......................... 436/548; 436/513; 436/526; 436/63
[58] Field of Search .............................. 436/513, 63, 526, 436/548

[56] References Cited

U.S. PATENT DOCUMENTS 4,849,337  7/1989  Calenoff et al. .
5,595,881  1/1997  Kendrick et al. .

OTHER PUBLICATIONS

Irsch et al., *Immunotechnology*, vol. 1, No. 2, pp. 115–125, Aug. 1995.

Oshiba et al., *Clin. Immunol. Immunopath.*, vol. 72, No. 8, pp. 342–349, Sep. 1994.

Donohue et al., *J. Allerg. Clin. Immunol.*, vol. 95, pp. 587–596, 1995.

*Primary Examiner*—Toni R. Scheiner
*Attorney, Agent, or Firm*—Cooley Godward LLP

[57] ABSTRACT

Methods and compositions are provided for the diagnosis of allergen hypersensitivity in a patient. Rare, allergen-specific cells are enriched from a complex cell population, e.g. a patient blood sample. The percentage of blood cells that bind to a particular allergen is less than 0.01%. The allergen-specific cell population is enriched by magnetic cell sorting. In normal blood, the allergen-binding cells are primarily B-cells expressing CD19 and CD21. In blood from allergic patients, an additional population of effector cells, e.g. basophilic granulocytes is labeled by the allergen.

6 Claims, 4 Drawing Sheets allergic donor

Parol (0.3%)
no stain

Parol (38.9%)
no stain normal donor

Parol (0.01%)
no stain

Parol (10.2%)
no stain

PBL → MACS enriched

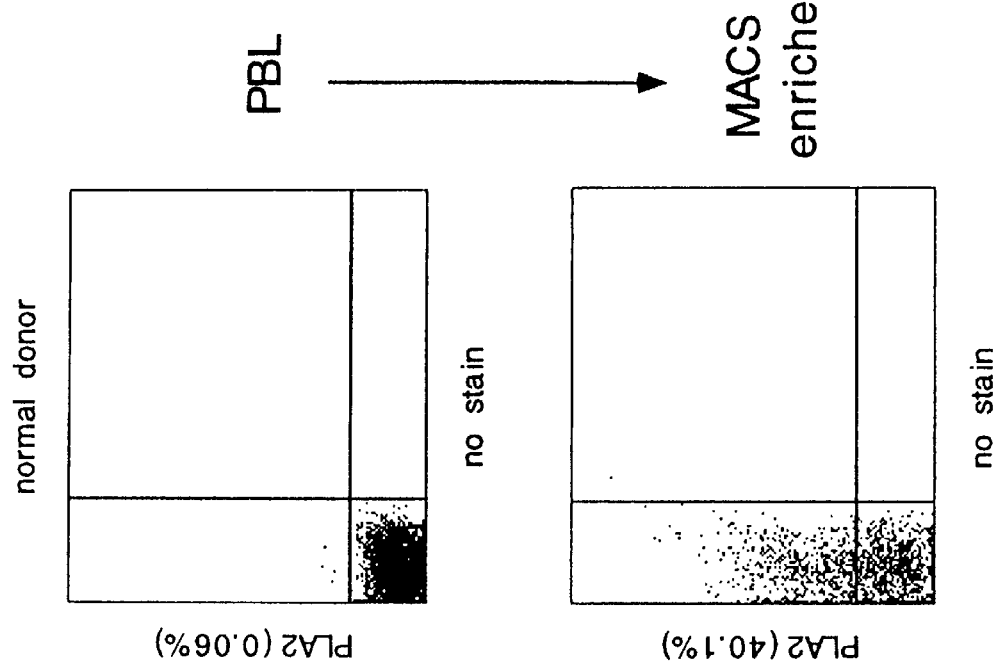
FIG. 2A
FIG. 2B
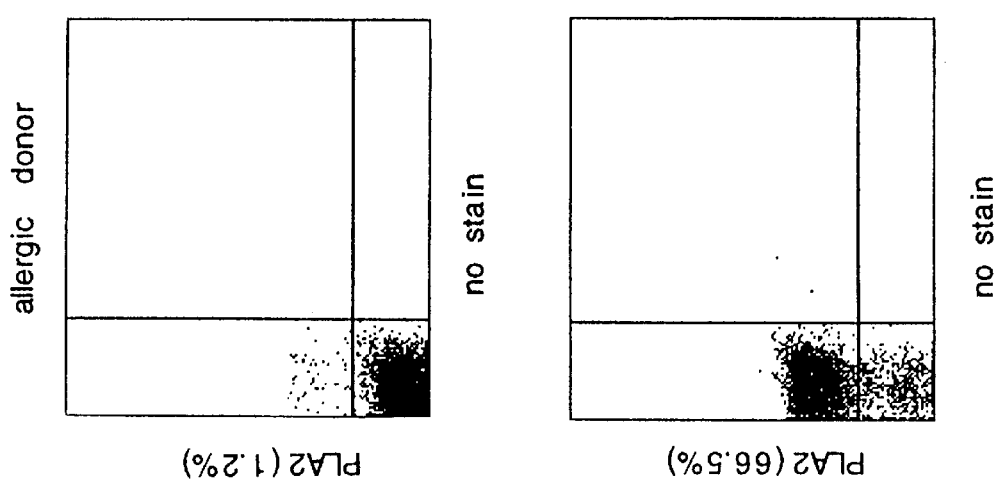

allergic donor normal donor

FIG. 4A
FIG. 4B
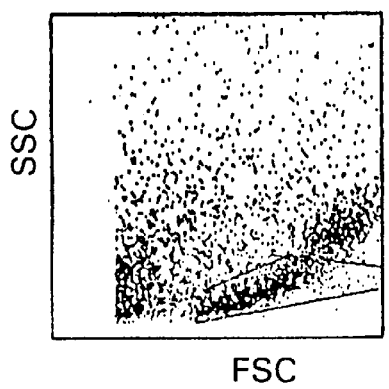
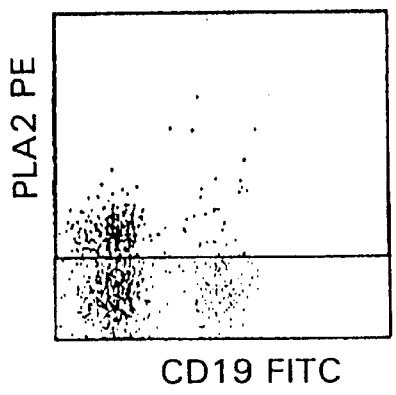
FIG. 4C
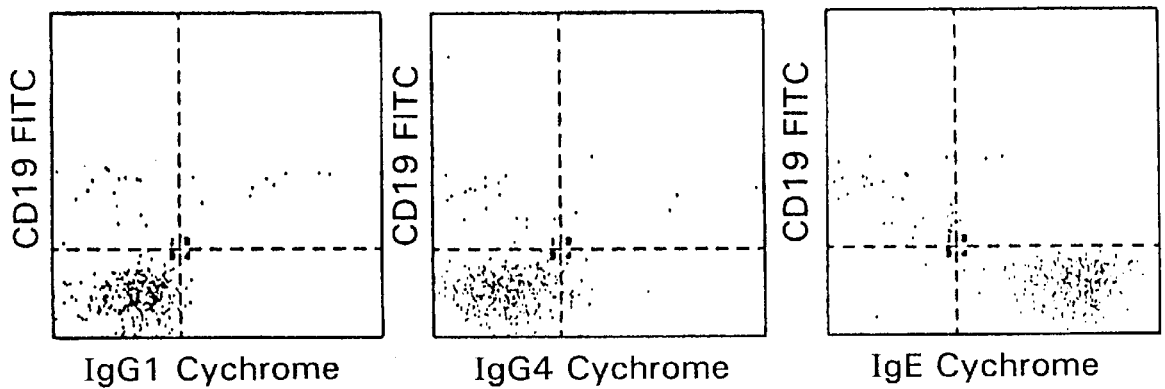

ISOLATION AND CHARACTERIZATION OF ALLERGEN-BINDING CELLS FOR DIAGNOSIS OF HYPERSENSITIVITY

CROSS-REFERENCE TO RELATED APPLICATIONS

This application is a continuation of U.S. Ser. No. 08/660,035, filed Jun. 6, 1996, now U.S. Pat. No. 5,786,161.

INTRODUCTION

Technical Field

The field of this invention is the diagnosis of allergen hypersensitivity.

Background

Allergy or hypersensitivity of the immune system in its different forms affects more than 20% of the human population. Man is a highly susceptible species to anaphylaxis. After sensitization with an allergen, a second exposure elicits constriction of the bronchioles, in some cases resulting in death from asphyxia. This allergic reaction is mediated by allergen-specific antibodies, mostly of the IgE class. The antibodies can be directed against a variety of antigens, such as molecules from pollen, fungi, food, house dust mite, hymenoptera venoms or animal danders.

The aggregation of mast cell and basophil high-affinity IgE receptors by IgE and antigen causes the release of mediators and cytokines, including heparin, eosinophil and neutrophil chemotactic factors, leukotrienes and thromboxanes. Immunoglobulin class switching to IgE expression is mediated by IL-4 or IL-13 and may be mediated through CD40 stimulation. These cytokines may be produced by T helper cells, or by activated mast cell/basophil like cells. Activation of mast cells can provoke an ongoing local allergic reaction as long as antigen confrontation is maintained.

Prophylactic treatment by hyposensitization, or avoidance of the allergen, requires identification of the specific allergen that is causing the hypersensitive condition. When allergen extracts are administered intradermally to detect or confirm the allergic status of a patient, an allergic patient will respond with an inflammatory reaction at the site of the injection However, this type of testing is unreliable, and causes significant patient discomfort. Methods of allergen testing that are less invasive would be highly desirable. In addition, the direct analytical and preparative assessment of cells that specifically bind with allergens would provide valuable diagnostic tools and greatly facilitate analysis of the human allergic response.

Relevant Literature

Miltenyi et al. (1990) *Cytometry* 11:231–236 describe the use of antibody conjugated superparamagnetic particles for separating rare cell populations. Oshiba et al. (1994) *Clin. Immunology and Immunopathology* 72:342–349 describe the isolation of B cells specific for tetanus toxin or KLH hapten by conjugating to magnetic particles. Donhoe et al. (1995), *J. Allergy Clin. Immunol.* 95:587–596 Analyze IgE+ cells in peripheral blood of atopic and hypersensitive donors by two- and three-color flow cytometry for B cell differentiation markers. Manz et al. (1995) *P.N.A.S.* 92:1921–1925 describe the analysis and sorting of cells according to secreted molecules that are trapped on the cell surface with an affinity matrix. Gross et al. (1995) *P.N.A.S.* 92:537–541 describe the analysis of rare cell populations using flow cytometry.

Surface phenotyping of basophils from peripheral blood on the basis of a negative reactivity with mixed antibodies to CD2, CD14, CD16, and CD19, analyzed by flow cytometry, is described in Takahashi et al. (1993) *J. Immunol Methods* 162:17–21. Mul et al. (1992) *J. Immunol Methods* 149:207–14 describe the purification of human basophilic granulocytes with immunomagnetic beads conjugated to monoclonal antibodies specific for CD2, CD14, CD16 and CD19.

Hoffman (1994) *Int. Arch. Allergy Immunol.* 104:184–190 provides the complete amino acid sequence of two vespid venom phospholipases. Oreste et al. (1991) *Int. Arch. Allergy Immunol.* 96:19–27 purify and characterize the major allergen of *Parietaria officinalis*. D'Amato et al. (1992) Allergy 47:443–449 review Parietaria pollinosis.

SUMMARY OF THE INVENTION

Methods and compositions are provided for the diagnosis of allergen hypersensitivity in a patient. The diagnosis utilizes a sample of patient hematopoietic cells, e.g. blood, and does not require invasive intradermal challenge. Specific allergen-binding cells are enriched from the sample by magnetic cell sorting. The diagnosis relies on differences in the composition of allergen-binding cells in allergic vs. normal individuals. In normal blood, the allergen-binding cells are primarily B-cells expressing CD19 and CD21. In blood from allergic patients, an additional population of basophilic granulocytes are labeled by the allergen. The presence of such basophilic granulocytes is indicative of a hypersensitive, IgE response. The enriched cell populations are further useful in the isolation and characterization of allergen-binding cells.

BRIEF DESCRIPTION OF THE DRAWINGS

FIGS. 2A and 2B show flow cytometry plots of $PLA_2$-binding cells from PBL of a normal donor (FIG. 2B) and an allergic donor (FIG. 2A) with the MiniMACs. The specific cells were tagged with digoxigenin-conjugated $PLA_2$ and labeled with anti-digoxigenin-microbeads and anti-digoxigenin-PE.

FIGS. 4A, 4B, and 4C show the phenotypic analysis of $PLA_2$-binding cells from an allergic donor. Positive cells are labeled with $PLA_2$-digoxigenin and stained with anti-digoxigenin-PE. Counterstainings are performed with anti-CD19-fluorescein isothiocyanate (FITC) and Cychrome-labeled anti-isotype antibodies. The first gate was set excluding dead cells and monocytes (FIG. 4A). The second gate was set on the $PLA_2$-binding, PE-stained cells (FIG. 4B). Gated cells were analyzed for surface immunoglobulin (FIG. 4C).

DESCRIPTION OF THE SPECIFIC EMBODIMENTS

Figure 1A:
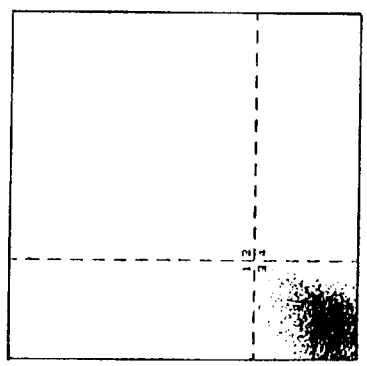
FIGS. 1A and 1B show flow cytometry plots of Paro 1-binding cells from peripheral blood leukocytes (PBL) of a normal donor (FIG. 1B) and an allergic donor (FIG. 1A) using the MiniMACs. The specific cells were tagged with digoxigenin-conjugated Paro1 and labeled with anti-digoxigenin-microbeads and anti-digoxigenin-phycoerythrin (PE).

Methods and compositions are provided for the diagnosis of allergen hypersensitivity in a patient. The diagnosis is performed using a patient test sample and does not require invasive intradermal challenge. Panels of allergens may be used. Differences in the composition and numbers of allergen binding cells in allergic vs. normal individuals provides the basis for diagnosis. Indirect or direct conjugates of a test allergen and selection reagent, e.g. magnetic particle, fluorochrome, etc. are used to select allergen-binding cells from the sample. In normal blood, the allergen-binding cells are primarily B-cells expressing CD19 and CD21. In blood from allergic patients an additional population of effector cells, including basophilic granulocytes, are labeled by the allergen. The enriched cell populations are further useful in the isolation and characterization of allergen-binding cells. The presence of specific allergen-binding basophilic granulocytes indicates hypersensitivity.

The subject methods are useful in the initial diagnosis of hypersensitivity, and can be further used in the staging of allergic disease and monitoring of therapy. In particular, evaluation of risk for anaphylactic shock, a life-threatening systemic reaction to allergen exposure, may be monitored. Because the subject methods analyze blood cells, the risk of systemic reaction can be directly correlated to a positive result. Evaluation of hyposensitization treatment may assess effector cells, e.g. basophils, eosinophils, etc., or memory B/plasma cells. Effector cell analysis may include quantitation and analysis of functional capacity. Memory B cell analysis evaluates allergen specific populations according to their surface Ig class, where a shift to IgG2 and other non-IL-4 induced Ig classes is indicative of successful treatment.

The test allergen is any antigen suspected of causing a hypersensitive immune response. As used herein, hypersensitive immune responses are those reactions of a mammalian immune system characterized by the production of high levels of IgE antibody. Contact with the allergen results in mast cell degranulation and release of histamines, heparin, eosinophil and neutrophil chemotactic factors, leukotrienes and thromboxanes, etc. Conventional tests for hypersensitivity include a skin test, where the allergen is injected intradermally. A hypersensitive response will cause rapid production of a wheal and erythema within 30 minutes.

Allergens of interest include antigens found in food, such as strawberries, peanuts, milk proteins, egg whites, etc. Other allergens of interest include various airborne antigens, such as grass pollens, animal danders, house mite feces, etc. Molecularly cloned allergens include *Dermatophagoides pteryonyssinus* (Der P1); Lol pI-V from rye grass pollen; a number of insect venoms, including venom from jumper ant *Myrmecia pilosula; Apis millifera* bee venom phospholipase A2 ($PLA_2$) and antigen 5S; phospholipases from the yellow jacket *Vespula maculifrons* and the white faced hornet *Dolichovespula maculata*; a large number of pollen proteins, including birch pollen, ragweed pollen, Paro1 (the major allergen of *Parietaria officinalis*) and the cross-reactive allergen Parjl (from *Parietaria judaica*), and other atmospheric pollens including *Olea europaea*, Artemisia sp., gramineae, etc. Other allergens of interest are those responsible for allergic dermatitis caused by blood sucking arthropods, e.g. Diptera, including mosquitos (Anopheles sp., Aedes sp., Cuffseta sp., Culex sp.); flies (Phlebotomus sp., Culicoides sp.) particularly black flies, deer flies and biting midges; ticks (Dermacenter sp., Ornithodoros sp., Otobius sp.); fleas, e.g. the order Siphonaptera, including the genera Xenopsylla, Pulex and Ctenocephalides. The specific allergen may be a polysaccharide, fatty acid moiety, protein, etc. In many cases the allergenic epitope has been shown to be a polypeptide. Pure allergen compositions may be isolated from natural sources, prepared by expression from recombinant DNA, or be obtained by other techniques well-known in the art.

The patient may be tested with one or a panel of suspected allergens. The determination of the specific allergen to which a patient is hypersensitive allows the affected individual to seek treatment, e.g. desensitization, and to avoid activities that increase risk, e.g. exposure to the allergen. Panels may include a number of different pollens, groups of suspected food allergens, animal allergens, etc. Samples may be run side by side, or in pools.

The subject methods are also used for the separation, culture and use of specific allergen-binding cells, e.g. B-cells, plasma cells and basophilic granulocytes. The granulocytes bind the allergen through IgE antibodies that are bound to Fc receptors on the cell surface. The enriched populations of allergen-binding B-cells are useful for producing allergen specific antibodies, particularly IgE antibodies. The enriched B-cells are immortalized by infection with Epstein-Barr virus or fusion with myeloma cell lines. Such B-cell lines produce allergen-specific human monoclonal antibodies, which can be used as reference reagents and for studies of repertoire and B-cell biology. The B-cells are valuable tools to unravel the role of specific B-lymphocytes in antigen presentation.

The test allergen may be directly or indirectly conjugated to a selection reagent. In one embodiment of the invention, the selection reagent is a magnetic reagent, such as a superparamagnetic microparticle (microparticle). Herein incorporated by reference, Molday (U.S. Pat. No. 4,452,773) describes the preparation of magnetic iron-dextran microparticles and provides a summary describing the various means of preparing particles suitable for attachment to biological materials. A description of polymeric coatings for magnetic particles used in high gradient magnetic separation (HGMS) methods are found in DE 3720844 (Miltenyi) and U.S. Pat. No. 5,385,707. Methods to prepare superparamagnetic particles are described in U.S. Pat. No. 4,770,183.

Direct conjugation of an allergen to a magnetic particle is achieved by use of various chemical linking groups. The polysaccharide or other coating of the microparticle is suitably derivatized to provide functional groups. A variety of such modifications is known in the art. Amino groups may be introduced before or after forming the beads. An aldehyde function may be introduced by reacting the polysaccharide with diimidazol or DCCD, and coupling hexane diamine to the sugar molecules. Alternatively, in preparing the dextran for coating, aminodextran may be mixed with unsubstituted dextran to provide amino groups. The polysaccharides may be conveniently oxidized using periodate to provide aldehyde functional groups that can be conjugated to amino substituents on a proteinaceous binding moiety, particularly under the conditions of reductive amination. Allergens can be coupled to the particles through side chain amino or sulfhydryl groups and heterofunctional cross-linking reagents.

A large number of heterofunctional compounds are available for linking to entities, Illustrative entities include: azidobenzoyl hydrazide, N-[4-(p-azidosalicylamino)butyl]-3'-[2'-pyridyldithio]propionamide), bis-sulfosuccinimidyl suberate, dimethyladipimidate, disuccinimidyltartrate, N-K-maleimidobutyryloxysuccinimide ester, N-hydroxy sulfosuccinimidyl-4-azidobenzoate, N-succinimidyl [4-azidophenyl]-1,3'-dithiopropionate, N-succinimidyl [4-iodoacetyl]aminobenzoate, glutaraldehyde, and succinimidyl 4-[N-maleimidomethyl]cyclohexane-1-carboxylate.

A preferred linking group is 3-(2-pyridyldithio)propionic acid N-hydroxysuccinimide ester (SPDP) or 4-(N-maleimidomethyl)-cyclohexane-1-carboxylic acid N-hydroxysuccinimide ester (SMCC) with a reactive sulfhydryl group on the antibody and a reactive amino group on the magnetic particle.

Alternatively, in a preferred method, the allergen is indirectly coupled to the magnetic particles. The allergen is directly conjugated to a hapten, and hapten-specific, second stage antibodies are conjugated to the particles. In this way, one magnetically coupled antibody preparation may be used with a variety of allergens. Suitable haptens include digoxin, digoxigenin, FITC, dinitrophenyl, nitrophenyl, avidin, biotin, etc. Methods for conjugation of the hapten to a protein, i.e. allergen, are known in the art, and kits for such conjugations are commercially available. Empirical binding assays may be performed to determine the optimal ratio of hapten to allergen for the subject analysis.

The anti-hapten antibodies may be polyclonal or monoclonal antibodies of various isotypes, e.g. IgM, IgA, IgG, usually of the IgG class. Antisera is commercially available from a variety of sources, or may be raised in any convenient animal, e.g. mouse, rat, sheep, goat, etc. The antibodies may be coupled as intact tetramers, or fragments thereof which maintain the specific binding portion of the molecule, e.g. Fab and $F(ab')_2$ fragments.

In an alternative embodiment, the selective reagent is a fluorochrome conjugated allergen. Suitable labels include fluorescein isothiocyanate (FITC), rhodamine, Texas Red, phycoerythrin, allophycocyanin, 6-carboxyfluorescein (6-FAM), 2',7'-dimethoxy-4', 5'-dichloro-6-carboxyfluorescein (JOE), 6-carboxy-X-rhodamine (ROX), 6-carboxy-2',4',7',4,7-hexachlorofluorescein (HEX), 5-carboxyfluorescein (5-FAM), N,N,N',N'-tetramethyl -6-carboxyrhodamine (TAMRA), etc. As described above, the allergen may be directly or indirectly labeled. Fluorochrome reagents are useful in panel reactivity assays, where a pool of two or more defined allergens, each conjugated to a different fluorochrome, is added to a sample. A number of pools may be typed at one time, permitting a range of allergens to be tested from a single blood draw.

A hematopoietic cell sample is taken from a patient suspected of having a hypersensitivity to the test allergen. Conveniently, blood samples are used. The term blood sample, as used herein, shall include hematopoietic biological samples such as blood, lymph, leukophoresis product, bone marrow and the like; also included in the term are derivatives and fractions of such fluids. The blood sample is drawn from any site, conveniently by venipuncture. Blood samples will usually be from about 1 to 100 ml of whole blood, i.e. from $10^5$ to $10^7$ nucleated blood cells, and may be treated with anticoagulants, e.g. heparin, EDTA, citrate, acid citrate dextrose or citrate phosphate dextrose, as known in the art. The sample may be subjected to treatment such as dilution in buffered medium, concentration, filtration, or other gross treatment that will not involve the destruction of allergen-binding cells.

The sample may be derived from any mammal, including primate, particularly human, murine, particularly mouse, equine, bovine, ovine, porcine, lagomorpha, canine, feline, etc.

A preparation of nucleated cells may be made from the sample using any acceptable procedure that can separate viable nucleated cells from erythrocytes. The use of whole blood allows detection of effector cells such as eosinophils, in addition to basophil detection. The use of Ficoll-Paque density gradients or elutriation is well documented in the literature. Alternatively, the blood cells may be resuspended in a solution which selectively lyses adult erythrocytes, e.g. ammonium chloride-potassium; ammonium oxalate, etc. Treatments may also include removal of cells by various techniques, including centrifugation, using Ficoll-Hypaque, panning, affinity separation, using antibodies specific for one or more markers present as surface membrane proteins on the surface of cells, or other techniques that provide for enrichment of leukocytes.

A directly coupled or haptenated allergen, as described above, is added to a cell sample. The amount of allergen necessary to bind a particular cell subset is empirically determined by performing a test separation and analysis. The amount will vary with the affinity of the allergen and the density of specific binding partner, e.g. membrane bound Ig or Ig bound to a surface Fc receptor. The cells and allergen are incubated for a period of time sufficient for complexes to form, usually at least about five minutes, more usually at least about 10 minutes, and usually not more than one hour, usually not more than about 30 minutes. If directly coupled allergen is used, the incubated mixture may be directly applied to a magnetic separation device. If haptenated allergen is used in the first binding step, then a magnetically coupled anti-hapten antibody is added in a second step, prior to applying the incubated mixture to the magnetic separation device.

While not necessary for the practice of the subject methods, it may be useful to label the cells with a fluorochrome, e.g. phycoerythrin, FITC, rhodamine, Texas red, allophycocyanin, etc. The fluorochrome label may be used to monitor microscopically or by flow cytometry the cell composition after the enrichment step. Fluorescent labeling may conveniently utilize the same indirect coupling system as the magnetic particles. For example, a hapten-coupled allergen, (e.g. digoxigenin-coupled allergen) may be used in combination with an anti-hapten antibody, (e.g. anti-digoxigenin antibody) coupled to magnetic particles, followed by labeling with a fluorochrome conjugated antibody directed to the anti-hapten antibody.

The medium in which the cells are separated will be one that maintains the viability of the cells. A preferred medium is phosphate buffered saline containing from 0.1 to 0.5% fetal calf serum. Various media are commercially available and may be used according to the nature of the cells, including Dulbecco's Modified Eagle Medium (dMEM), Hank's Basic Salt Solution (HBSS), Dulbecco's phosphate buffered saline (dPBS), RPMI, Iscove's medium, phosphate buffered saline (PBS) with 5 mM EDTA, etc., frequently supplemented with fetal calf serum, bovine serum albumin (BSA), human serum albumin (HSA), etc.

Exemplary magnetic separation devices are described in WO/90/07380, PCT/US96/00953 and EP 438,520, herein incorporated by reference. In a preferred embodiment, an improvement is provided by the use of a high gradient magnetic matrix of closely packed ferromagnetic spheres in place of the prior art matrix of steel wool, wires, etc. The spheres will be usually at least about 200 Tm in diameter and not more than about 1000 Tm in diameter, more usually at least about 250 Tm in diameter and not more than about 300 Tm in diameter. For optimum performance it is preferred that the composition of spheres be generally homogeneous in size, usually varying not more than about 15% from the average size.

The spheres are composed of a ferromagnetic material (e.g. iron, steel, etc.), which may be coated with an impermeable coating to prevent the contact of cells with metal. By impermeable coating it is meant a polymeric coating which contains substantially less than 30% water by weight, which does not permit the passage of ions, and which is formed on the sphere as a result of passive application, cross-linking or polymerization of a relatively hydrophobic polymer or co-polymer. Suitable polymers include polystyrenes, polyacrylamides, polyetherurethanes, polysulfones, fluorinated or chlorinated polymers such as polyvinyl chloride, polyethylenes and polypropylenes, polycarbonates and polyesters, etc.

The matrix of spheres should have adequate surface area to create sufficient magnetic field gradients in the separation device to permit efficient retention of magnetically labeled cells. The volume necessary for a given separation may be empirically determined, and will vary with the cell size, antigen density on the cell surface, antibody affinity, etc. The flow rate will be determined by the size of the column, but will generally not require a cannula or valve to regulate the flow.

The labeled cells are retained in the magnetic separation device in the presence of a magnetic field, usually at least about 100 mT, more usually at least about 500 mT, usually not more than about 2T, more usually not more than about 1T. The source of the magnetic field may be a permanent or electromagnet. After the initial binding, the device may be washed with any suitable physiological buffer to remove unbound cells.

The bound cells are released from the magnetic separation means by removing the magnetic field, and eluting in a suitable buffer. The cells may be collected in any appropriate medium, preferably one that maintains the viability of the cells. Various media are commercially available and may be used according to the nature of the cells, including dMEM, HBSS, dPBS, RPMI, PBS-EDTA, PBS, Iscove's medium, etc., which may be supplemented with-fetal calf serum, BSA, HSA, etc. The cells may then be used as appropriate for diagnosis or antibody production.

Where the sample is bound to a fluorochrome selective reagent, flow cytometry or microscopy may be used to detect the presence of B cells and/or effector cells labeled with the allergen. Such methods are practiced as known in the art.

The subject methods provide for an enriched population of allergen-specific cells, including B-cells, basophilic granulocytes, eosinophils and plasma cells. In a non-allergic patient test sample, the number of allergen-binding cells in the enriched population may be low, due to the small absolute number of cells present in the starting population. In an allergic patient test sample, the number of allergen-specific cells present in the enriched population will usually be about 20%, and in some cases may be as high as 90%. The purity may be evaluated by various methods. Conveniently, flow cytometry may be used in conjunction with light-detectable reagents specific for cell surface markers expressed by leukocytes.

For a diagnosis of hypersensitivity, the enriched cell population is analyzed for the presence of effector cells, e.g. allergen-binding basophilic granulocytes. Such analysis may be performed on slides, with a Coulter counter, or by flow cytometry. The expression of cell surface markers such as CD38, CD25, CD7 (described in Kepley et al. (1995) *J. Immunol.* 154:6548–6555) or CD9 is characteristic of basophilic granulocytes. The cells may also be characterized by staining with May-Gruenwald/Geimsa reagents, as known in the art. Histamine release is also used to detect basophils. Quantitative methods for histamine release detection include microdialysis (Peterson et al. (1992) *J. Allergy* 47:635–637); HPLC (Leino et al. (1990) *Agents Actions* 31:178–182); immunoassay (Hammar et al. (1990) *J. Immunol. Methods* 128:51–58); microfibre method (Nolte et al. (1987) *Allergy* 42:366–373), etc.

In an allergic patient, at least about 50% of the allergen-binding cells will be effector cells such as basophilic granulocytes, and may be as high as 90% of the allergen-binding cells. In a non-allergic patient, less than about 10% of the allergen-binding cells are basophilic granulocytes. A positive diagnosis of allergy to a specific antigen is made when the basophil population is increased relative to a control sample. The number of basophils may be at least about twice that of a normal, non-allergic donor in a similarly treated sample, and may be as high as about ten times the number of basophils in a control sample.

Allergen-binding B-cells from the enriched cell population, particularly B cells from human donors, may be used to produce allergen-specific antibodies. The B cells may be immortalized through infection with Epstein-Barr virus, fusion with a myeloma cell line, transfection with a transforming retrovirus, etc. to produce a monoclonal cell line. Screening for cell lines that produce allergen-specific antibodies is performed by any convenient method, e.g. ELISA, RIA, etc. to determine allergen specificity. B-cells that produce monoclonal IgE are of particular interest for the production of testing reagents, etc.

A kit may be provided for the practice of the subject invention. For example, the kit may include one or a panel of hapten-conjugated allergens (for example a series of digoxigenin-coupled pollen, insect and/or food allergens), and either magnetic particles conjugated to anti-hapten antibodies or fluorescent labeled anti-hapten antibodies. The kit may further comprise a means for magnetic separation, and buffers and other reagents used in the separation process.

The following examples are offered by way of illustration and not by way of limitation.

EXPERIMENTAL

Materials and Methods

Antigens and preparation of conjugates. Phospholipase A2 from bee venom was purchased from Sigma, Freiburg, Germany (P 9279). Paro1 was purified as described in Oreste et al. (1991) *Int. Arch. Allergy Immunol.* 96:19–27. Both allergens were conjugated to digoxigenin (dig), using the DIG antibody labeling kit from Boehringer Mannheim, FRG. Preparations were made at different protein to digoxigenin molar ratios, and tested by titration on peripheral blood mononuclear cells (PBMC) for their ability to stain specifically a distinct population of the PBMC, but not monocytes or macrophages.

Cells. Blood was obtained from normal donors (blood bank of the University of Cologne) or from allergic patients with a known history of severe allergy either against bee venom or *Parietaria officinalis*. Nearly all of the allergic patients had elevated levels of allergen-specific IgE serum antibodies. Patients allergic against bee venom all showed a positive reaction in skin tests performed to confirm the diagnosis.

Magnetic and fluorescent labeling of cells with antigen. Blood samples were diluted with two volumes of RPMI, and aliquots of 30 ml were layered onto 15 ml of Ficoll-Hypaque (Pharmacia, Freiburg, FRG). After centrifugation (for 20 minutes at room temperature, 800 g) cells at the interphase were collected and washed three times with cold phosphate buffered saline (PBS). Cells were resuspended in a small volume of PBS/0.5% BSA/10 mM EDTA, and incubated for 10 minutes on ice with 5 mg/ml of the murine monoclonal antibody A20/44 (IgG$_1$) to block nonspecific binding. Allergen-digoxigenin conjugates were added at 10 Tg/ml and the cells were incubated for another 10 minutes. After washing with PBS/BSA/EDTA, the cells were then incubated (for 10 minutes at room temperature) with superparamagnetic microbeads coupled to anti-digoxigenin antibodies (Miltenyi Biotec, Bergisch-Gladbach, Germany), making a ⅕ dilution of microbeads to cell suspension. Finally, the cells were stained with ⅟₅₀ volume of Streptavidin-PE-coupled anti-digoxigenin antibodies by incubation for 10 minutes on ice, and finally washed again. Prior to magnetic separation, the cells were deaggregated by passage through a 40 Tm nylon-mesh (Partec, Munster, FRG0).

Antigen-specific magnetic cell sorting. Magnetic isolation was performed essentially as described in Miltenyi et al. (1990) *Cytometry* 11:231–236. Magnetic separation Mini-MACs columns (Miltenyi Biotec, GmbH) were prewashed with 4 ml of degassed PBS/BSA. Half of the cell sample was loaded onto the column, the column was washed, and the other half of the sample was applied. Then, the columns were washed with 5 ml PBS/BSA. Cells which had bound to the allergen-digoxigenin conjugate, and thereby bound the antibody-coupled magnetic microbeads, were retained in the separation column in the presence of a magnetic field. To elute the retained cells, the columns were removed from the magnetic field and the cells were washed from the column with 1 ml of PBS/BSA. The separation procedure was monitored by flow cytometry using a FACScan and FACScan Research or Cellquest software (Becton Dickinson, San Jose, Calif.). For cytometric analysis, 10 Tg/ml of propidium-iodide (PI) was added in order to identify dead cells not only according to forward versus side scatter, but also according to relative F2 versus F3 fluorescence.

Immunofluorescence. The following antibodies were used for immunophenotyping: ICD3, ICD5, ICD10, ICD14, ICD16, ICD19 (described in Allison and Lanier (1987) *Ann. Rev. Immunol.* 5:503–540; Gadol and Ault (1986) *Immunol. Rev.* 93:24–34; Pezzutto et al. (1987) *J. Immunol.* 138:2793–2799; Perussia et al. (1984) *J. Immunol.* 133:180–189; Bhan et al. (1981) *J. Exp. Med.* 154:180) conjugated to fluorescein isothiocyanate (FITC), or phycoerythrin (PE), all obtained from Beckton Dickinson. ICD9, ICD21, ICD23, ICD38, (described in Nadler et al. (1983) *J. Immunol.* 131:244–250; Tedder et al. (1984) *J. Immunol.* 133:678–683; Thorley-Lawson et al. (1985) *J. Immunol.* 134:3007–3012; Uchiyama et al. (1981) *J. Immunol.* 126:1398–1403) were all obtained from Immunotec (Dardilly, France) as FITC-conjugates. The isotype-specific antibodies were all purchased as biotin (Bio)-, or horseradish-peroxidase (HRPO) conjugates. IIgG1-Bio, IIgG4-Bio, IIgE-Bio, IIgG-HRPO, IIgM-HRPO, IIgE-HRPO, IKappa-HRPO, ILambda-HRPO were obtained from SBA, (Birmingham, Ala.). IDigoxigenin-beads and IDigoxigenin-PE were obtained from Miltenyi Biotec (Bergisch Gladbach, FRG). Streptavidin-Cychrome was purchased from Pharmingen (San Diego).

Generation of EBV-lines. Feeder cells were generated from autologous PBMC by depletion of B-lymphocytes with ICD19-superparamagnetic microbeads and high gradient magnetic cell sorting using an A2 column (Miltenyi Biotec, Bergisch Gladbach, FRG) with a 0.4 Tm needle. The negative cells were incubated for 30 minutes at 37° C. with 50 Tg/ml mitomycin C (Medac, Hamburg, FRG). To remove excess mitomycin before adding the feeder cells to the sorted cells, the prospective feeder cells were washed three times in 50 ml of RPMI, supplemented with 5% FCS. After the last washing step, T-lymphocytes were suppressed by adding 1 Tg/ml cyclosporin A (Sandoz, Basel, Switzerland), and cultured in the medium described below. EBV-lines were generated from the antigen positive fractions of the magnetic sorts by incubating 100–1000 cells per well in 96-well flat bottom plates (Costar, Mass., USA) with ¼ volume of supernatant of the EBV secreting marmoset cell line B95-8 (Miller and Lipman (1973) *P.N.A.S.* 70:190–194). These cells were layered onto $2 \times 10^5$ autologous feeder cells per well, generated from PBMC as described above, cultured in RPMI with 10% FCS, 50 U/ml penicillin, 50 Tg/ml streptomycin, and 2 mM L-glutamine. After two weeks, aggregates representing the progeny of single cells were picked under the microscope and diluted over a series of wells. For most of the lines generated this way, monoclonality was later confirmed by restriction analysis of JH-rearrangements.

Western Slot Blots. Different amounts of unconjugated PLA$_2$, or bovine serum albumin (BSA) as negative control, were blotted onto nitrocellulose-filters (Hybond C extra, Amersham, Braunschweig, FRG), using a micro-sample-filtration manifold (Schleicher-Schuell, Dassel, FRG). After washing with PBS, the filters were blocked for one hour with Trizma-Base, NaCl, pH 7.6 containing 3% Tween 20 (TBS) (Serra, Heidelberg FRG), and 5% milk powder. The culture supernatants of the EBV-lines generated were deaggregated and sterilized by filtration, diluted with one volume of TBS/Tween/milk powder and applied to the filters. After incubation for one hour, filters were washed three times for five minutes in TBS/Tween20. Then the filters were incubated with HRPO-conjugates of antibodies, specific for the various human isotypes and diluted in TBS/Tween/drymilk, for 40 minutes at room temperature. After washing, as described before, filter-bound HRPO was quantitated using the ECL-System (Amersham, Braunschweig, FRG). Autoradiographs were obtained on X-OMAT-AR-films (Eastman-Kodak, New York, USA).

DARIA (double antibody radioimmunoassay). The DARIA was essentially carried out as described in Platts-Mills et al. (1978) *J. Immunol.* 120:1201–1210. For the determination of Paro1 specific human IgE or IgG; 50 Tl of supernatant from EBV-lines were mixed with 50 Tl of an appropriate dilution of an IgE or IgG myeloma protein. This solution was incubated for four hours at room temperature with 100 Tl of borate buffered saline (BBS, pH 8.0) containing 1 ng of radiolabeled Paro1 (10–20,000 cpm). Antigen-antibody complexes were precipitated by addition of an appropriate amount of goat anti-human IgE or IgG for 16 hours at 4° C. Precipitates were collected on Whatman GF/A filters. After washing the filters in 10 ml of BBS, the bound radioactivity was determined in a gamma counter.

Amounts of antibodies were expressed as: $((a-b)/(B_{max}-b)\%)$, where a=cpm bound by the tested supernatant, b=background cpm (cpm bound by a pool of sera without IgE against Paro1) and $B_{max}$=cpm bound by the positive reference serum pool (a pool of sera with high levels of Paro1 specific IgE). Supernatants binding less than 1.3× background cpm were considered negative.

May-Gruenwald-/Giemsa-staining After MACS-separation, the fractions enriched for allergen-binding cells were resuspended in 300 Tl of RPMI 1640 supplemented with 30% FCS and collected by centrifugation for 10 minutes at 400 g at 4° C. The pellets were resuspended in 100 Tl RPMI/30%/FCS. Cytospins were prepared in a Cytospin centrifuge (Shahdon-Elliott), spinning the cells onto the slides at 1000 rpm for three minutes. The cytospin preparations were air-dried overnight at room temperature. The slides were then incubated for five minutes in May-Gruenwald solution (Merck, Darmstadt, FRG), followed by incubation in a 1:1 dilution of May-Gruenwald:Weisebuffer for another five minutes. The final staining step was carried out by immersing the slides in a 1:10 dilution of Giemsa solution (Merck Darmstadt, FRG) in water for 15 minutes. The slides were then washed in distilled water and air dried for 30 minutes. Finally, the preparations were embedded in Eukitt (Kindler Freiburg, FRG), and covered with a cover glass, and analyzed in a Zeiss Axiolab microscope.

Results

Figure 1A:
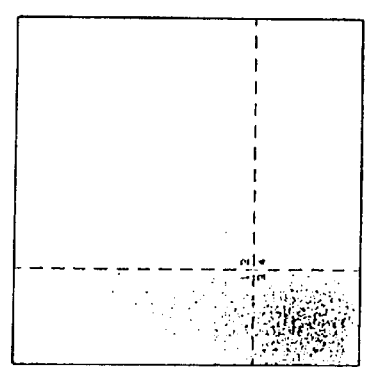
Figure 1B:
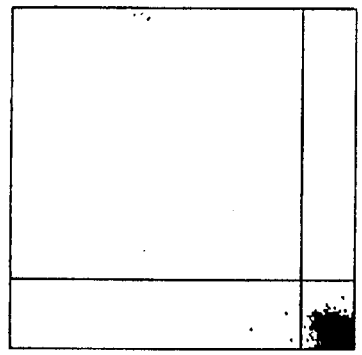
Figure 1B:
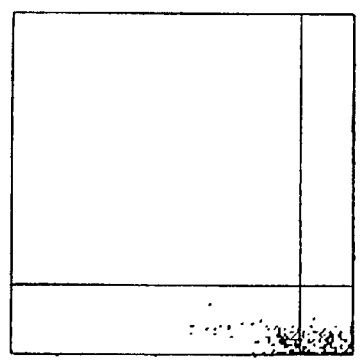

Enrichment of allergen-binding cells. For the isolation of allergen-binding cells from peripheral blood (50 ml from allergic donor or 500 ml from normal donors), the blood was depleted of erythrocytes, neutrophils and eosinophils on a Ficoll-gradient. The mononuclear cells were then stained with digoxigenin-conjugates of either $PLA_2$ or Paro1, anti-dig-MACS microbeads and anti-dig-antibodies conjugated to phycoerythrin. As determined by flow-cytometry, the frequency of allergen-binding cells was below 0.1% in the blood of normal donors, whereas samples from allergic donors contained between 0.4% and 2.3% of allergen-binding cells before MACS-separation. The percentages of allergen-binding cells were calculated by analysis of 100,000 events by FACS. The allergen-binding cells were enriched by high gradient magnetic cell sorting with the MiniMACS to frequencies of up to 75% (allergic donors) and 2–45% (non-allergic donors). The data are shown in FIGS. 1 and 2. From some allergic donors (50 ml of blood), up to $8 \times 10^5$ allergen-binding cells, mostly basophilic granulocytes were enriched, with only 3–11% B-cells. From the blood of normal donors (500 ml), at most $6 \times 10^5$ allergen-binding cells were enriched, nearly all of them B-lymphocytes.

Phenotype of the allergen-binding cells. The indirect staining of the digoxigenin-conjugated allergen with anti-dig-PE was used to monitor the magnetic cell sortings. It also allowed the phenotypical analysis of the sorted allergen-binding cells by multiparameter flow cytometry. The cells were counterstained with fluorescein- and CyChrome-conjugated antibodies specific for various surface markers, with the remaining PE-negative cells serving as an internal control. The allergen-binding cells from both normal and allergic donors did not express CD3, CD14 or CD16, markers for T-cells, monocytes or NK-cells. The frequency of labeled cells was very low. Cell types known for their ability to bind fluorochrome conjugates non-specifically were not enriched by the procedure.

Figure 3A:
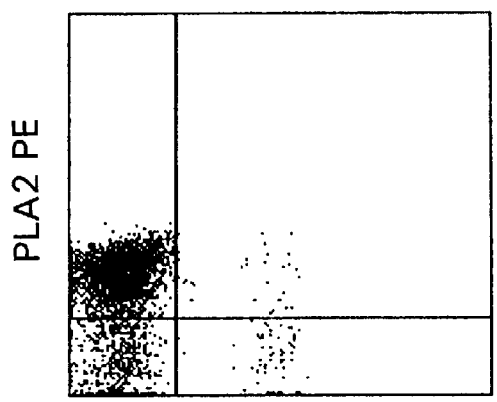
FIGS. 3A and 3B show counterstaining of the MACs-enriched $PLA_2$-binding cells from an allergic donor (FIG. 3A) and a normal donor (FIG. 3B) with antibodies directed against a B-cell marker (CD19) or against a marker for basophilic granulocytes and plasma cells (CD38).
Figure 3A:
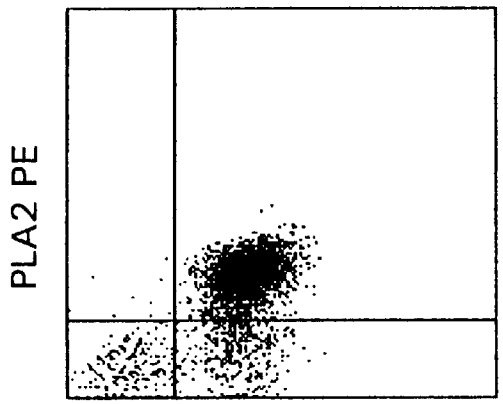
Figure 3B:
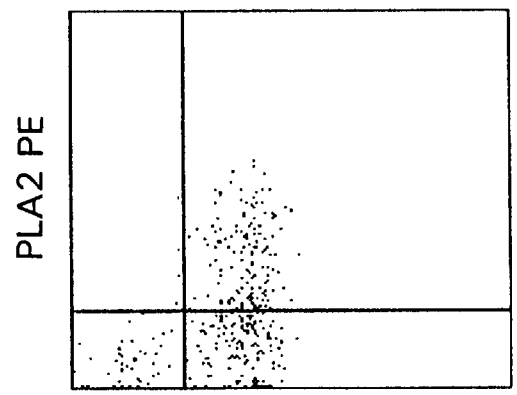
Figure 3B:
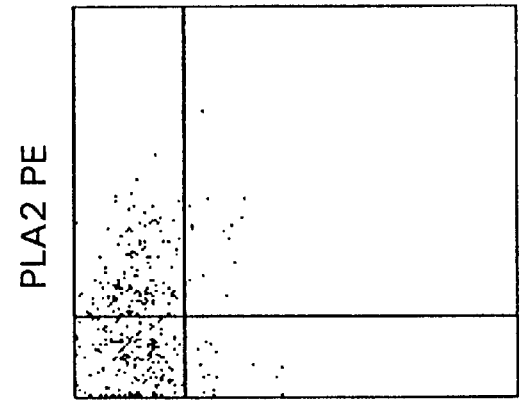

A drastic difference was observed when comparing allergen-binding cells from the blood of allergic and non-allergic donors with respect to the expression of CD19, a B-cell marker, and CD38, a marker of plasma cells and basophilic granulocytes. The absolute numbers of allergen-binding CD19$^+$ B-cells were about the same. However, about 90% of the allergen-binding cells enriched from the blood of normal donors, but only 3–12% from allergic donors are CD19$^+$ B-cells. The data are shown in FIG. 3. Almost all of these cells also express CD21, the receptor for EBV, making them a suitable target for transformation and to generate allergen-specific B-cell lines. These results are summarized in Table 1.

TABLE 1

|  | normal donor | | | | allergic donor | | | |
| --- | --- | --- | --- | --- | --- | --- | --- | --- |
|  | 1 | 2 | 3 | 4 | Z1 | ET | BO | GA |
| before MACS | 0.02% | 0.1% | 0.03% | 0.08% | 1.89% | 1.75% | 0.68% | 0.36% |
| after MACS | 12.2% | 18.2% | 4.7% | 45.8% | 92.2% | 44.8% | 60.0% | 23.8% |
| CD38 | 3.0% | 9.1% | 12.1% | 9.6% | 93.2% | 72.0% | 90.9% | 82.0% |
| CD19 | 95.1% | 82.0% | 78.5% | 97.7% | 2.8% | 11.8% | 7.5% | 11.3% |
| Ratio CD19/ CD21 | 90.0% | 81.2% | 71.5% | 95.3% | 2.6% | 12.1% | 6.2% | 10.7% |

The numbers show the percentages of $PLA_2$-binding cells from blood of normal and allergic donors before and after enrichment with MACS. For phenotypical analysis the $PLA_2$-specific cells were counterstained with anti-CD38-FITC or anti-CD19-FITC. The results of a three color analysis, staining the cells with $PLA_2$-PE, anti-CD19-Cychrome and anti-CD21-FITC are also shown.

The majority of the enriched allergen-binding cells from blood of allergic donors stain positively for CD38, a marker expressed primarily on plasma cells and basophilic granulocytes. These cytometric analyses together with the May-Gruenwald/Giemas staining, clearly identify these cells as basophilic granulocytes. They represent approximately 72–95% of the enriched, allergen-binding cells, whereas in the case of normal blood donors only a few of these cells are observed. The specific antigen-receptor of basophilic granulocytes is most likely a Fc-receptor-bound immunoglobulin. Accordingly, nearly all of the allergen-binding CD38$^+$ cells stain for surface IgE, some also for IgG4, but none for IgG1 (shown in FIG. 4). Some of the enriched allergen-binding cells were transformed with Epstein-Barr virus. Three EBV-lines produce IgG, and two lines produce IgM specific for $PLA_2$, as was determined by Western Blot. Several lines produce Paro1-specific antibodies, as determined in Paro1-specific double antibody radio immunoassay (DARIA). Out of 25 EBV-lines tested, six produced Paro1-specific IgE, and several others produced different IgG-subclasses.

It is evident from the above results that the subject invention provides a rapid method for isolating allergen-binding cells from normal or allergic patient test samples. In the blood of allergic individuals, a high number of CD38-expressing allergen-binding cells are found. By May-Gruenwald and Giemsa staining, they are identified as basophilic granulocytes, which also stain with CD9, and weakly with CD25. The clear staining of basophilic granulocytes offers new means of allergy diagnosis and monitoring. The cellular analysis of the reactive effector cells has clear advantages over the commonly used provocation tests, since it does not have the side effects and risks for the patients. Furthermore, this technique provides more detailed information about the cell subsets and relative numbers of allergen-binding cells.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto, such as the use of any suitable separation means, without departing from the spirit or scope of the appended claims.

What is claimed is:

1. A method of producing allergen-specific monoclonal antibody, the method comprising:
   a. combining a hematopoietic cell sample with a test allergen directly or indirectly coupled to a magnetic microparticle;
   b. passing said cells through a magnetic field;
   c. removing unbound cells; and
   d. collecting bound cells in the substantial absence of said magnetic field to provide an enriched cell sample comprising allergen binding cells;
   e. immortalizing B-cells in said enriched cell sample; and
   f. screening said immortalized B-cells for cells that produce allergen-specific antibody.

2. The method of claim 1, wherein said allergen-specific antibody is an IgE antibody.

3. The method of claim 1, wherein said hematopoietic cell sample is a blood sample.

4. The method of claim 1, wherein said allergen is a protein.

5. The method of claim 4, wherein said protein is conjugated to a hapten, and anti-hapten antibody conjugated to a magnetic microparticle is included in said combining step.

6. The method of claim 1, wherein said immortalizing step comprises infection with Epstein-Barr virus.

* * * * *